(12) United States Patent
Bremer

(10) Patent No.: US 9,987,150 B2
(45) Date of Patent: Jun. 5, 2018

(54) ATTACHMENT SYSTEM FOR PROSTHETIC DEVICE

(71) Applicant: ADVANCED SUSPENSION SYSTEMS, LLC, Augusta, GA (US)

(72) Inventor: Arthur M. Bremer, Aiken, SC (US)

(73) Assignee: Advanced Suspension Systems, LLC, Augusta, GA (US)

( * ) Notice: Subject to any disclaimer, the term of this patent is extended or adjusted under 35 U.S.C. 154(b) by 13 days.

(21) Appl. No.: 14/896,541

(22) PCT Filed: May 27, 2014

(86) PCT No.: PCT/US2014/039550
§ 371 (c)(1),
(2) Date: Dec. 7, 2015

(87) PCT Pub. No.: WO2014/197236
PCT Pub. Date: Dec. 11, 2014

(65) Prior Publication Data
US 2016/0135968 A1    May 19, 2016

Related U.S. Application Data

(60) Provisional application No. 61/832,244, filed on Jun. 7, 2013.

(51) Int. Cl.
*A61F 2/76* (2006.01)
*A61F 2/80* (2006.01)
*A61F 2/78* (2006.01)

(52) U.S. Cl.
CPC .............. *A61F 2/76* (2013.01); *A61F 2/7812* (2013.01); *A61F 2/80* (2013.01); *A61F 2002/7818* (2013.01)

(58) Field of Classification Search
CPC .. A61F 2/76; A61F 2/7812; A61F 2/80; A61F 2002/7862; A61F 2002/30474
See application file for complete search history.

(56) References Cited

U.S. PATENT DOCUMENTS 1,507,998 A    9/1924   Hoare et al.
2,489,291 A    11/1949  Henschke et al.
(Continued)

OTHER PUBLICATIONS

International Search Report dated Oct. 16, 2014, from corresponding International Application No. PCT/US2014/039550 filed May 27, 2014, 9 pages.
(Continued)

*Primary Examiner* — Thomas J Sweet
*Assistant Examiner* — Melissa Hoban
(74) *Attorney, Agent, or Firm* — Meunier Carlin & Curfman LLC

(57) ABSTRACT

The present invention is directed to prosthetic device for attaching a mechanical limb to a user. The prosthetic device includes a liner, a prosthetic socket worn over the liner and an attachment mechanism. The attachment mechanism includes a belt that is guided over rollers coupled to the outside of the socket. A portion of the belt passes from the outer surface of the socket to the inner surface of the prosthetic socket to contact and matingly engage the liner, thereby fixing the position of the prosthetic socket with respect to the liner and the users limb.

19 Claims, 8 Drawing Sheets

(56) References Cited

U.S. PATENT DOCUMENTS

| | | | |
|---|---|---|---|
| 2,559,044 A | | 7/1951 | Pace et al. |
| 2,710,974 A | | 6/1955 | Motis |
| 3,599,245 A | | 8/1971 | Blatchford |
| 4,074,367 A | | 2/1978 | Loveless |
| 5,211,667 A | * | 5/1993 | Danforth ............... A61F 2/7812 623/33 |
| 5,895,429 A | * | 4/1999 | Cool ......................... A61F 2/64 623/27 |
| 6,793,682 B1 | * | 9/2004 | Mantelmacher ...... A61F 2/7812 623/33 |
| 2002/0077705 A1 | * | 6/2002 | Perkins ..................... A61F 2/78 623/36 |
| 2005/0049719 A1 | * | 3/2005 | Wilson ................... A61F 2/605 623/27 |
| 2005/0209706 A1 | * | 9/2005 | Warila ...................... A61F 2/78 623/33 |
| 2010/0198361 A1 | | 8/2010 | Warila |
| 2010/0274364 A1 | | 10/2010 | Pacanowsky et al. |
| 2011/0071647 A1 | | 3/2011 | Mahon |
| 2011/0313544 A1 | | 12/2011 | Perkins et al. |
| 2012/0041567 A1 | | 2/2012 | Cornell |
| 2014/0005798 A1 | * | 1/2014 | Bache ...................... A61F 2/80 623/33 |
| 2014/0249649 A1 | * | 9/2014 | Berschinski ............. A61F 2/78 623/35 |

OTHER PUBLICATIONS

International Preliminary Report on Patentability and Written Opinion dated Dec. 17, 2015, from corresponding International Application No. PCT/US2014/039550 filed May 27, 2014, 8 pages.

* cited by examiner

ATTACHMENT SYSTEM FOR PROSTHETIC DEVICE

CROSS-REFERENCE TO RELATED APPLICATIONS

This application claims benefit of U.S. Provisional Application No. 61/832,244, filed Jun. 7, 2013, which is hereby incorporated herein by reference in its entirety.

TECHNICAL FIELD

This invention relates to generally to prosthetics, and more particularly to a device and method for attaching a prosthetic device to a user's residual limb.

BACKGROUND

Different methods and devices have been used to retain and suspend a prosthetic device to an individual's residual limb. Belts, straps, harnesses, suction liners and other similar methods have been used in an attempt to fix the position of the prosthetic device with respect to the limb. There is a need in for an improved attachment method preventing longitudinal and rotational movement of the limb within the prosthetic device while providing comfort and individualized fit to the user.

SUMMARY

The present invention is directed to a device and method for attaching a prosthetic device to a user's residual limb. An aspect of the present disclosure is directed to a prosthetic device including a liner, a prosthetic socket, and an attachment mechanism. The liner may be sized and configured to be worn over a user's residual limb. The prosthetic socket may be sized and configured to be worn over the liner. The attachment mechanism may comprise a belt guided over rollers located on an outer surface of the prosthetic socket. A portion of the belt may pass from the outer surface of the prosthetic socket to an inner surface of the prosthetic socket and into contact with the liner. The belt may matingly engage the liner to fix the position of the prosthetic socket with respect to the liner.

Another aspect of the present disclosure is directed to a method of applying prosthetic device to a limb of a patient. The method may include applying a liner over the residual limb of the patient. The prosthetic socket may be applied over at least a portion of the liner. The prosthetic socket may include an attachment mechanism comprising a belt. The belt may pass from an outer surface of the prosthetic socket to an inner surface of the prosthetic socket. A portion of the belt may matingly engage a portion of the liner to fix a position of the prosthetic socket with respect to the liner.

The details of one or more embodiments of the invention are set forth in the accompanying drawings and the description below. Other features, objects, and advantages of the invention will be apparent from the description and drawings, and from the claims.

DESCRIPTION OF DRAWINGS

The device is explained in even greater detail in the following drawings. The drawings are merely examples to illustrate the structure of preferred devices and certain features that may be used singularly or in combination with other features. The invention should not be limited to the examples shown.

Like reference symbols in the various drawings indicate like elements.

DETAILED DESCRIPTION

Figure 1:
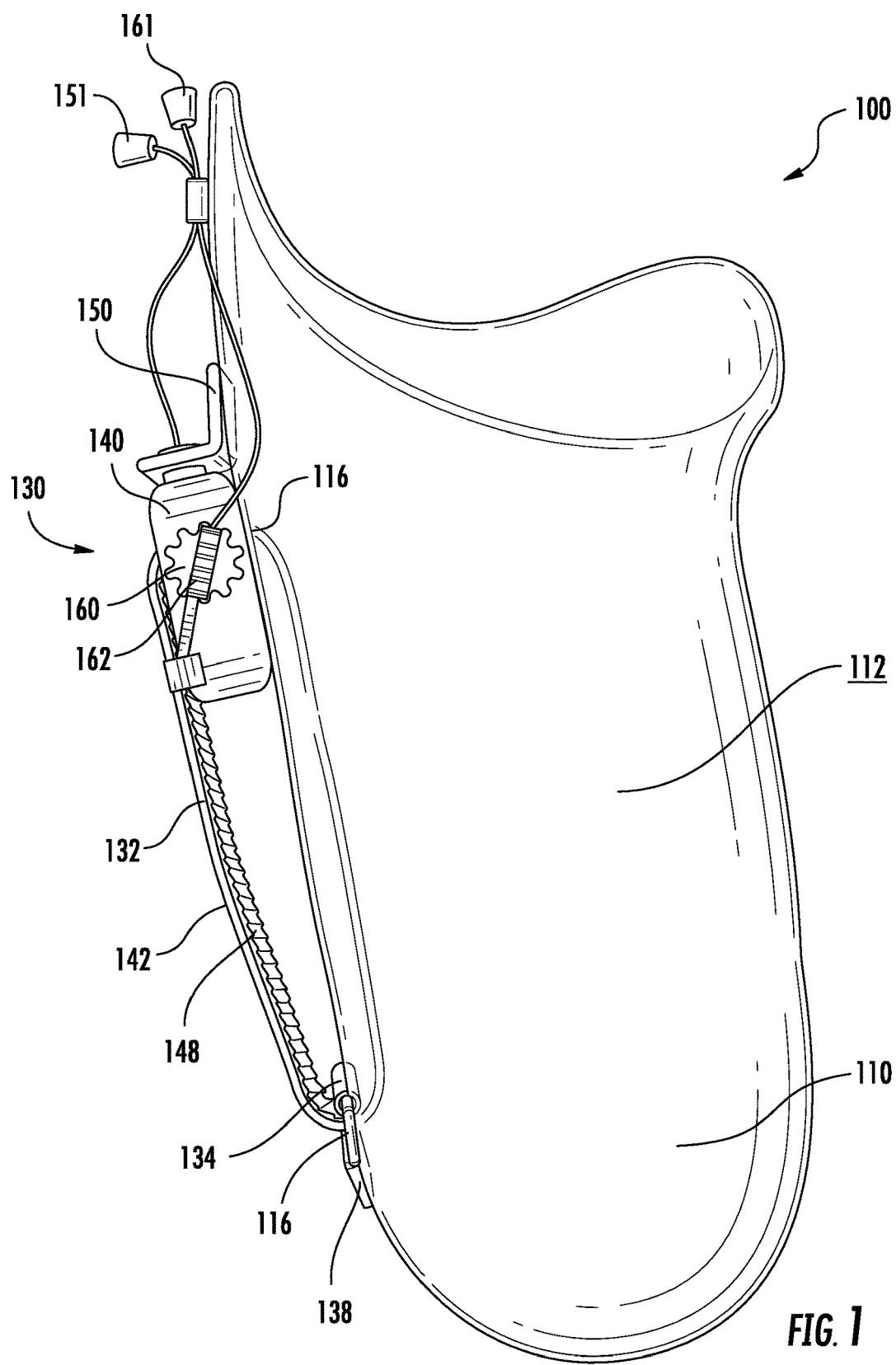
FIG. 1 is a back plan view of an example prosthetic socket.

Certain terminology is used in the following description for convenience only and is not limiting. The words "right", "left", "lower", and "upper" designate direction in the drawings to which reference is made. The words "inner", "outer" refer to directions toward and away from, respectively, the geometric center of the described feature or device. The words "distal" and "proximal" refer to directions taken in context of the item described and, with regard to the instruments herein described, are typically based on the perspective of the user wearing the prosthetic device. The terminology includes the above-listed words, derivatives thereof, and words of similar import.

In addition, various components may be described herein as extending horizontally along a longitudinal direction and lateral direction, and vertically along a transverse direction. Unless otherwise specified herein, the terms "lateral", "longitudinal", and "transverse" are used to describe the orthogonal directional components of various items. It should be appreciated that while the longitudinal and lateral directions are illustrated as extending along a horizontal plane, and that the transverse direction is illustrated as extending along a vertical plane, the planes that encompass the various directions may differ during use. Accordingly, the directional terms "vertical" and "horizontal" are used to describe the components merely for the purposes of clarity and illustration and are not meant to be limiting Certain examples of the invention will now be described with reference to the drawings. In general, such embodiments relate to a prosthetic device 100 for attachment to the residual limb of a user.

Figure 2:
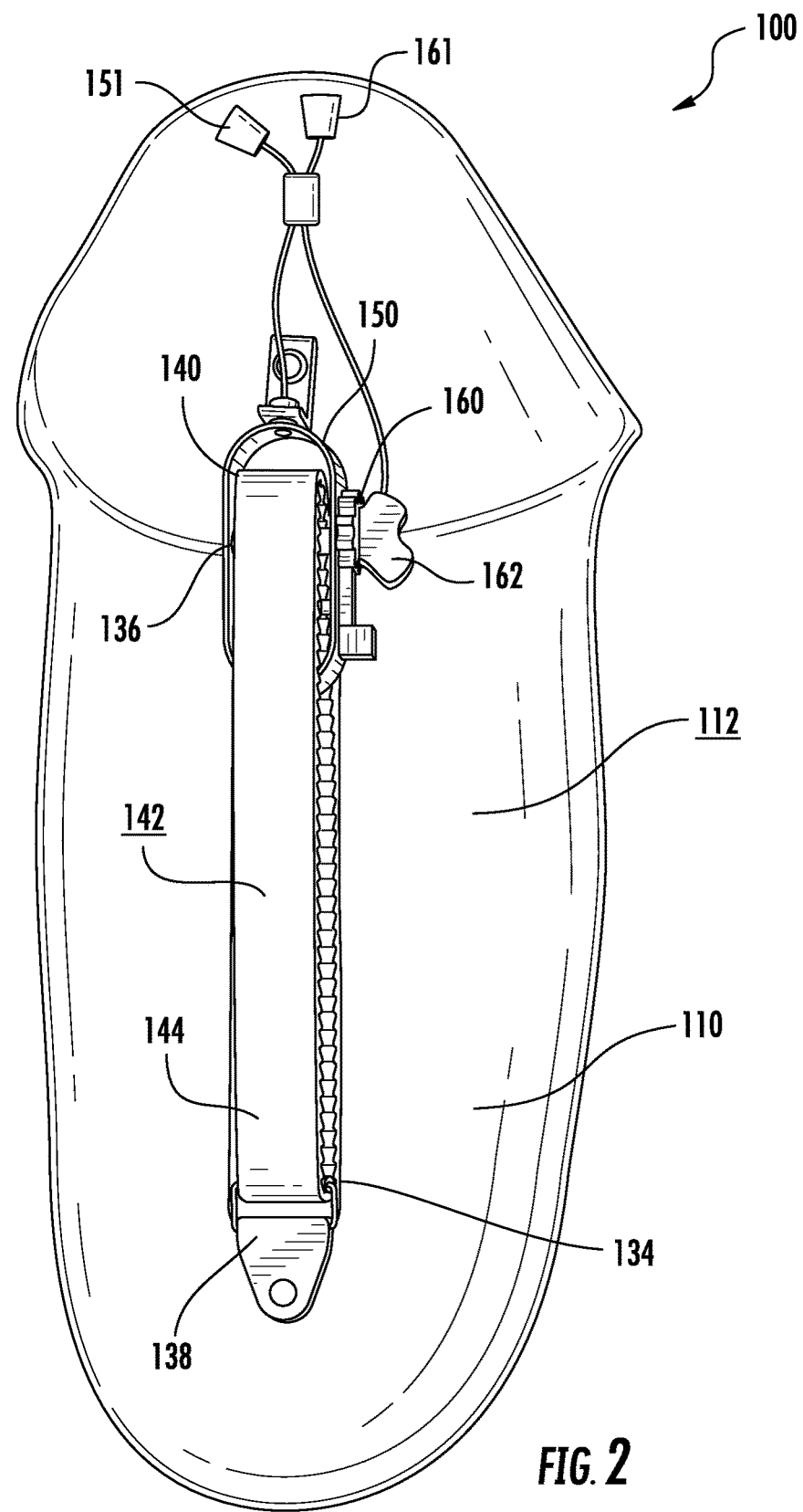
FIG. 2 is a side plan view of an example prosthetic socket
Figure 3:
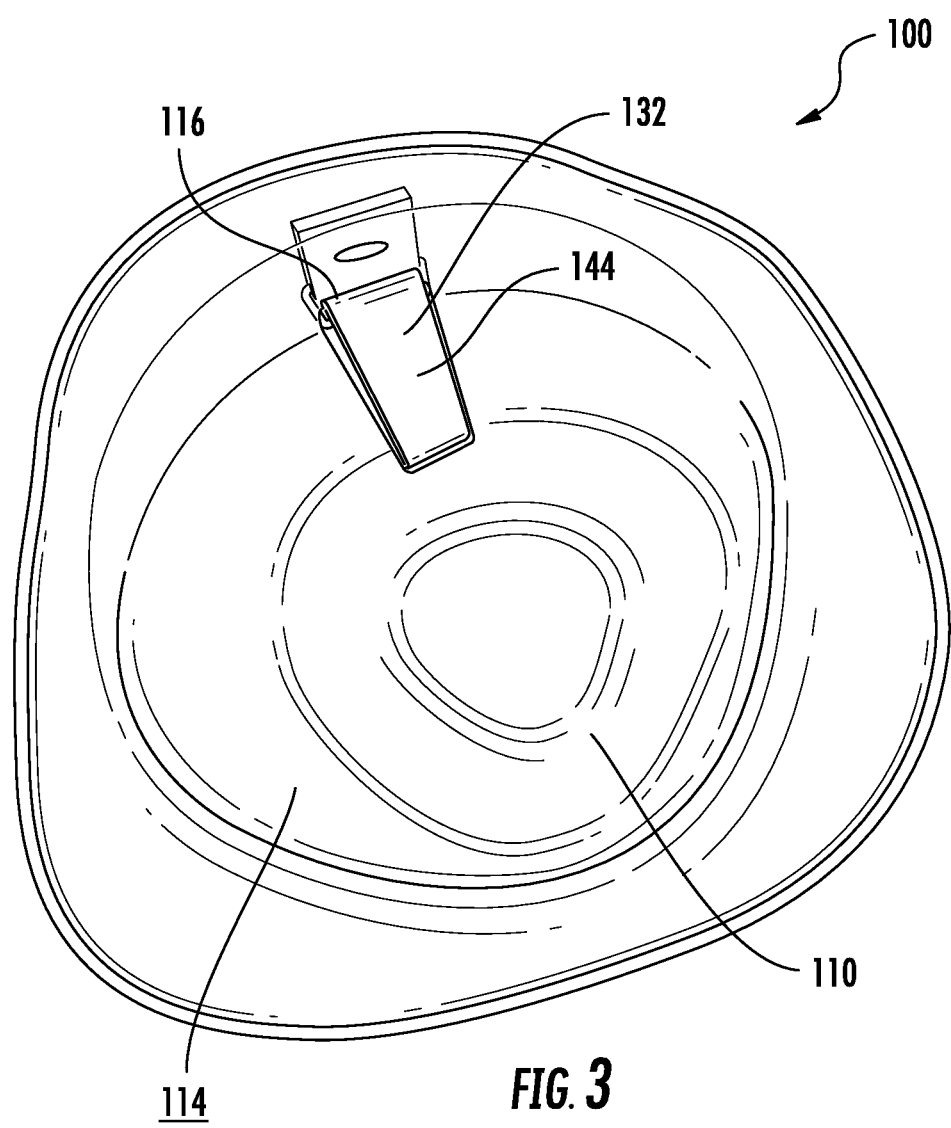
FIG. 3 is a top plan view of an example prosthetic socket.

FIGS. 1-3 are back, side and top views of an example prosthetic socket 110. The prosthetic socket 110 is configured to be worn on the user's residual limb. The distal end of the socket 110 can be coupled with a mechanical limb including, for example, a lower extremity mechanical prosthesis such as a transfemoral (above the knee) and/or transtibial (below the knee) prosthesis. It is also contemplated that the prosthetic device 100 and socket 110 can be configured for use with an upper extremity mechanical prosthesis such as a transhumeral (above the elbow) and/or transradial (below the elbow) prosthesis.

The socket 110 may be formed from a hard and/or rigid material. For example, the socket 110 may be formed from a hard plastic. The socket 110 can also be constructed from a material that provides for limited flexibility/deformation. An example socket 110 can be sized and configured to correspond to the size and shape of the user's residual limb. For example, the socket 110 can be formed to correspond to the muscle and bony prominences of the user's residual limb. The socket 110 can be sized and configured to correspond to a substantial portion of the user's residual limb such that sufficient contact is maintained between the socket 110 and the limb to support and facilitate the user's normal use and movement of the limb.

Figure 4:
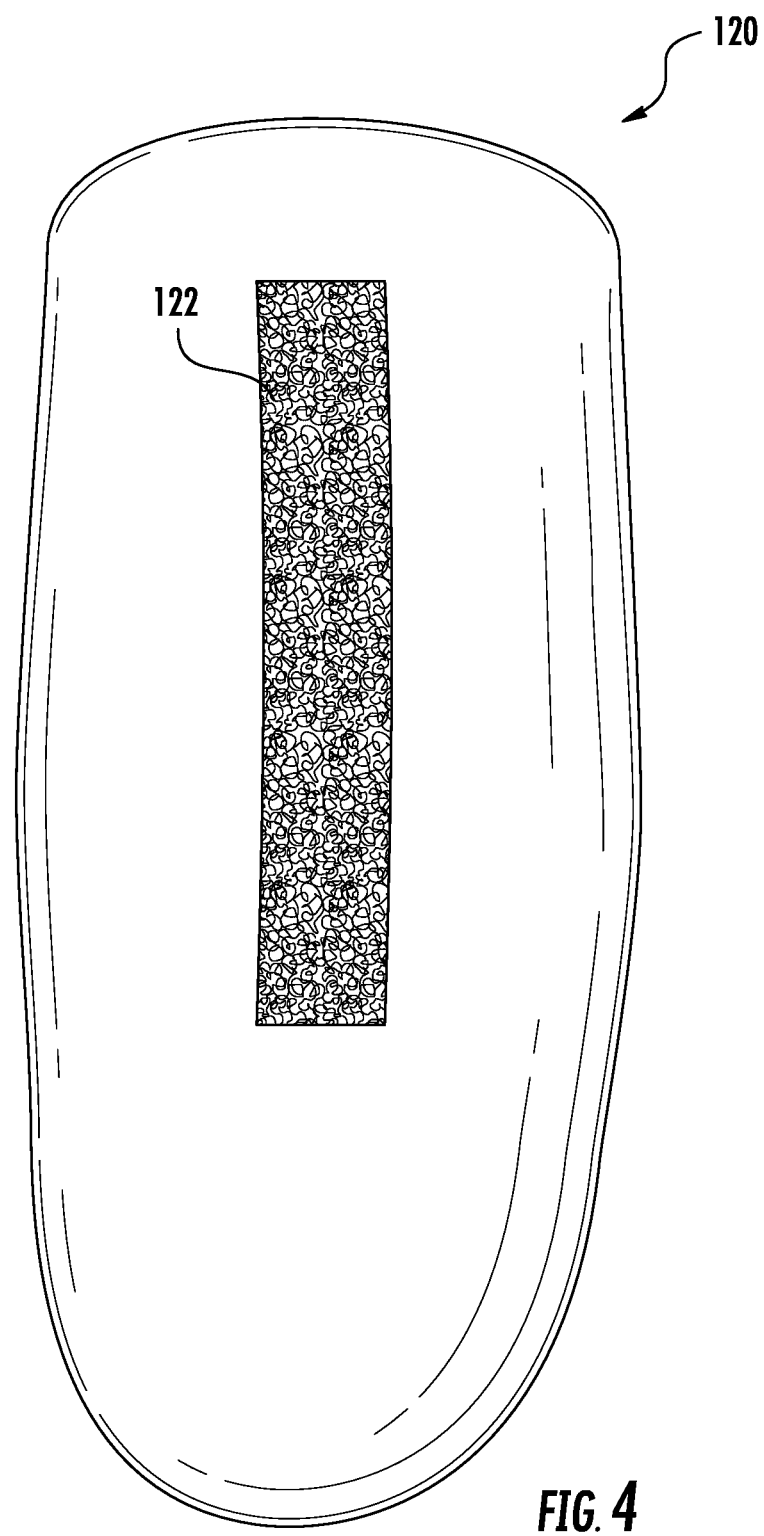
FIG. 4 is a side plan view of an example liner.

In an example prosthetic device 100, the socket 110 can be worn over a liner 120. The liner 120 can be formed of a biocompatible material such as neoprene or nonporous polyurethane. The liner 120 can be worn on the residual limb to provide slight compression, suction, and/or gripping connection between the inner surface of the liner 120 and the skin of the residual limb. The outer surface of the liner 120 can provide an interface for mating with the socket 110. For example, the outer surface of the liner 120 can include a mechanical fastener such as a hook/eye, buckle, toggle, button, string/lace, press stud, zipper, or any other form of mechanical connection/fastener known in the art to operatively couple a liner 120 to a socket 110. As illustrated in FIG. 4, the liner 120 can include a fastener material 122 for mating with a corresponding fastener material associated with the attachment mechanism 130. An example fastener material can include a hook and loop material such as VELCRO.

As provided in FIGS. 1-3 and 5, the prosthetic device 100 can include an attachment mechanism 130 coupled to the outer surface 112 of the socket 110. The attachment mechanism 130 can include a belt 132 guided over a first roller 134 and a second roller 136. The attachment mechanism 130 can vary in size and configuration according to the muscle/skeletal needs of the user. For example, an attachment mechanism 130 used with an average adult sized prosthetic device 100 can be about 8 inches long and about 2 inches wide. The first roller 134 and the second roller 136 can be about ⅜ inches in diameter and about 1½ inches long and the corresponding first and second roller housings 138, 140 can be about 1 inch long and about 2 inches wide.

The belt 132 can include an outside surface 142 including a fastener material 144 corresponding to the fastener material 122 of the liner 120 such that fastener material 144 of the belt 132 matingly and releasably engages the fastener material 122 of the liner 120. For example, fastener material 144 may include a hook and loop material such as VELCRO.

A portion of the belt 132 passes from the outer surface 112 of the socket 110 to the inner surface 114 of the socket 110. For example, the socket 110 can include openings 116 to provide the belt 132 access to the interior and inner surface 114 of the socket 110. The openings 116 can have a round or elongated shape. In another example, the openings 116 can have a square, rectangular, elliptical, or any other regular or irregular shape. The portion of the belt 132 within the socket 110 can contact and matingly engage the liner 120. The engagement between the belt 132 and the liner 120 can fix the position of socket 110 with respect to the liner 120. For example, when the belt 132 matingly engages the liner 120, the position of the socket 110 with respect to the liner 120 can be fixed in a longitudinal direction. Engagement between the belt 132 and the liner 120 can also fix the rotational position of the socket 110 with respect to the liner 120.

As outlined above, the attachment mechanism 130 can be coupled to the outer surface 112 of the socket 110. For example, the first roller 134 and second roller 136 of the attachment mechanism 130 can be coupled to a corresponding first roller housing 138 and second roller housing 140. In one example (not shown) both the first and second roller housings 138, 140 are fixedly be coupled to the outer surface 112 of the socket 110. In another example, illustrated in FIGS. 1-3 and 5, the first roller housing 138 is fixedly coupled to the outer surface 112 of the socket 110 and the second roller housing 140 is coupled to a tension member 150 such that the location of the second roller housing 140 with respect to the socket 110 is adjustable using the tension member 150. As illustrated, the second roller housing 140 is movable in a longitudinal direction along the socket 110.

Figure 5:
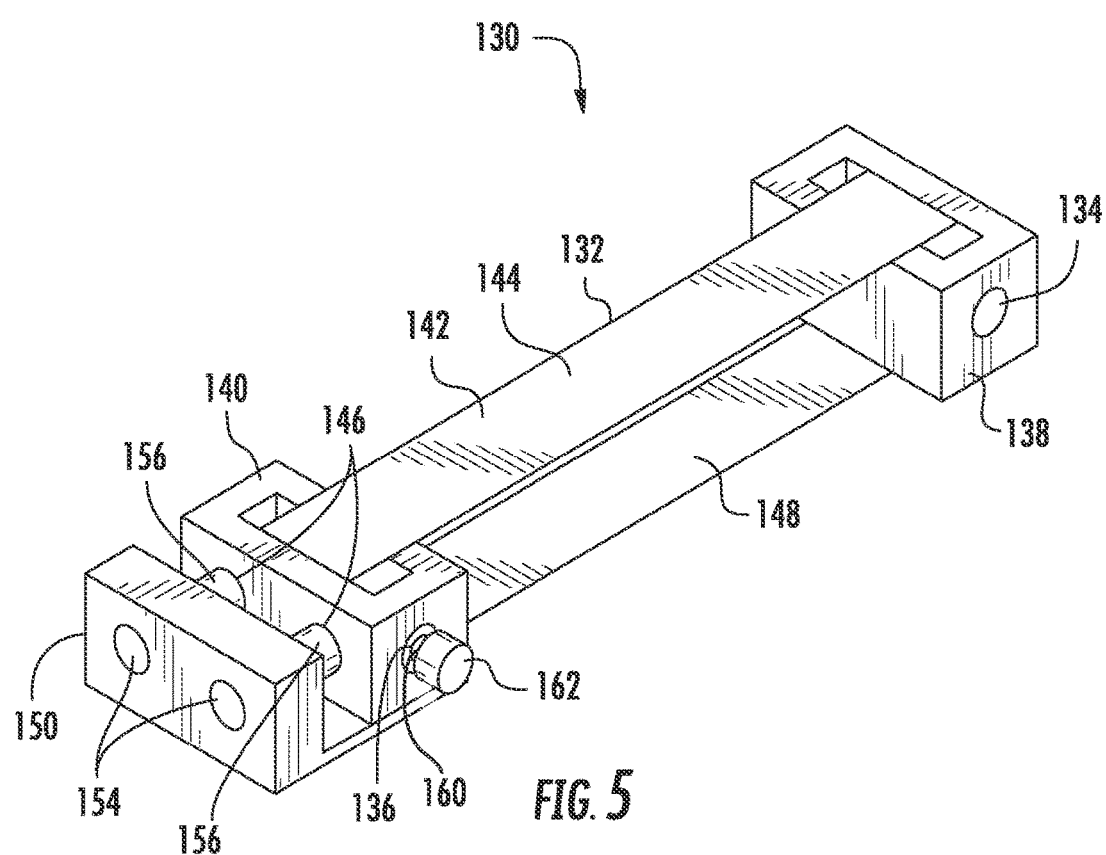
FIG. 5 is a perspective view of an example attachment mechanism
Figure 6:
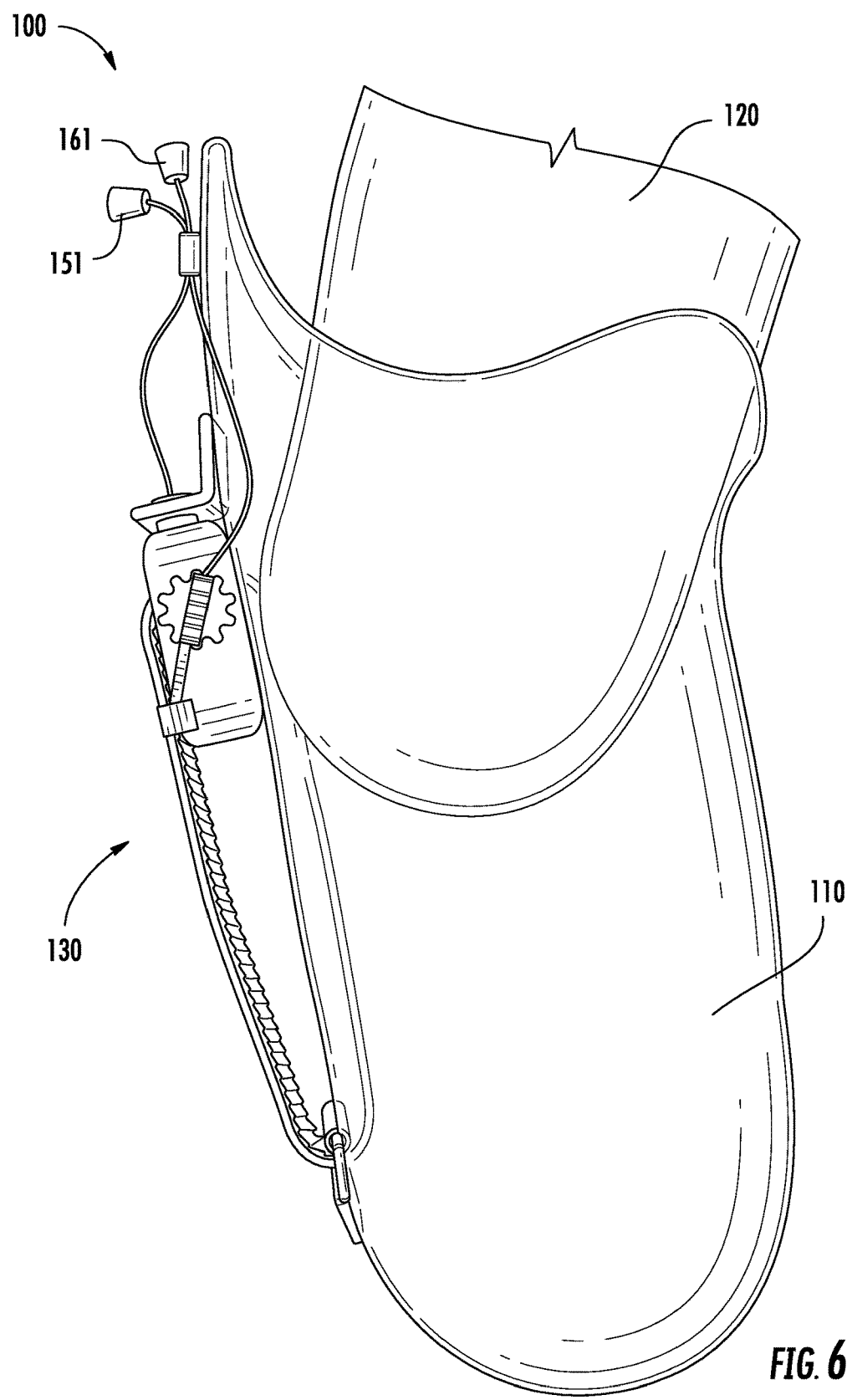
FIG. 6 is a perspective view of an example prosthetic socket and liner.
Figure 7:
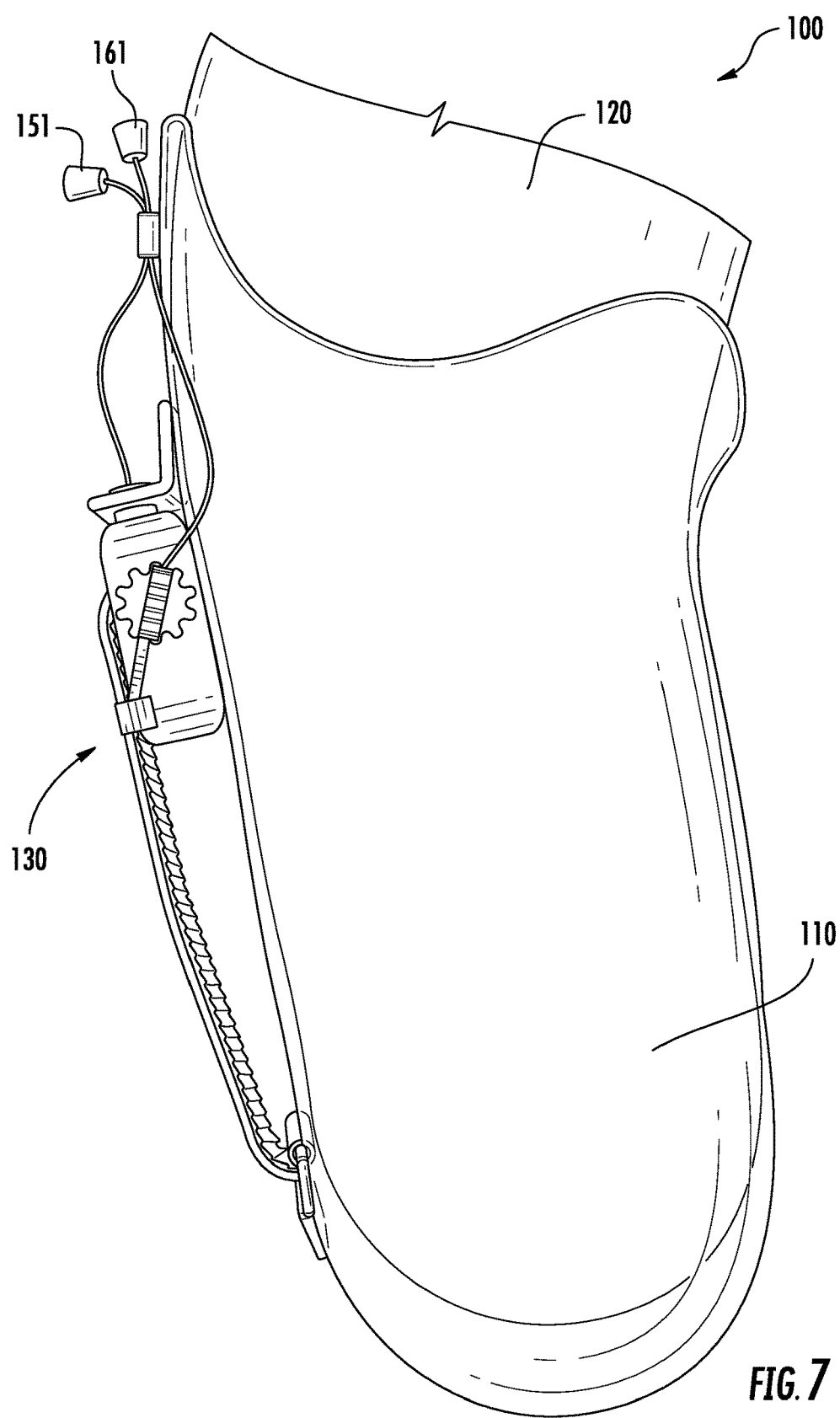
FIG. 7 is a back plan view of an example prosthetic device.
Figure 8:
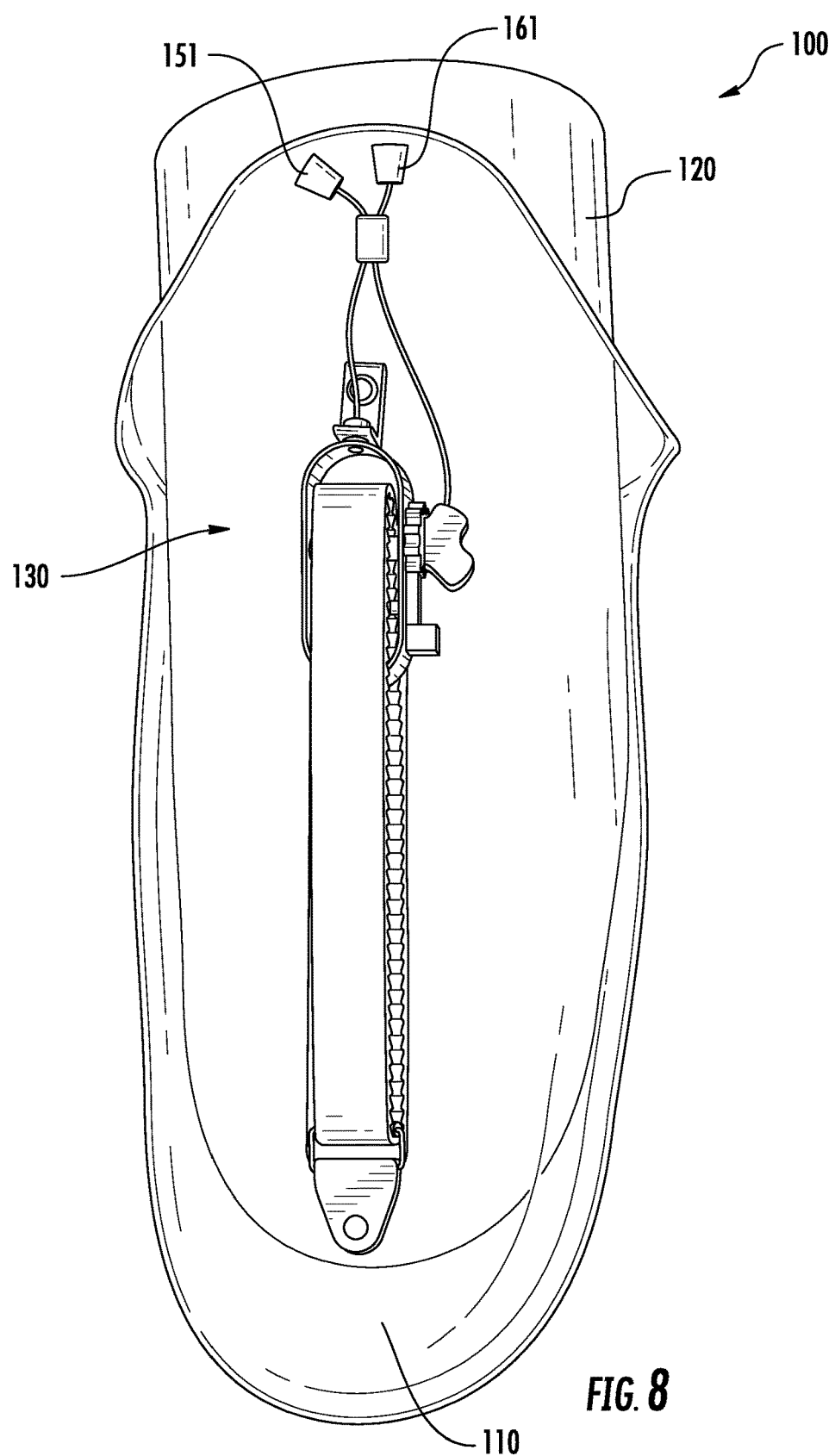
FIG. 8 is a side plan view of an example prosthetic device.

As illustrated in FIG. 5, the tension member 150 can include a tension base 152 and a coupler 154. The base 152 can be fixedly coupled to the outer surface 112 of the socket 110. The coupler 154 can matingly engaged the base 152. For example, a portion of the coupler 154 can be fixedly engaged in the longitudinal direction with respect to the base 152. The coupler 154 can engage the second roller housing 140 to adjust the longitudinal distance between the first and second roller housings 138, 140. For example, the coupler 154 include a threaded shaft 156 that matingly engages a corresponding threaded bore 146 in the second roller housing 140. The coupler 154 can rotate within the base 152 causing the threaded shaft 156 to engage the threaded bore 146 of the second roller housing 140 thereby adjusting the location of the second roller housing 140 with respect to the base 152.

The coupler 156 can be adjusted to reduce the longitudinal distance between the base 152 and the second roller housing 140, thereby increasing the distance between the first and second rollers 134, 136 and the corresponding first and second roller housings 138, 140. By increasing/decreasing the distance between the first and second rollers 134, 136 the force applied on the belt 132 can be adjusted. For example, by increasing the distance between the first and second rollers 134, 136 the tensile force on the belt 132 is increased. Similarly, by adjusting the distance between the first and second rollers 134, 136 the position of the belt 132 with respect to the liner 120 can be adjusted. For example, by adjusting the distance between the first and second rollers 134, 136, and thereby adjusting the force applied to the belt 132, can cause the belt 132 to move along the first and second rollers 134, 136. In moving the belt 132 along the rollers a new portion of the outside surface 142 of the belt comes into contact with the liner 120 resulting in the new portion of the belt 132 to matingly engage the liner 120. Accordingly, the user can adjust the location of the socket 110 with respect to the liner 120 and/or fix the position of the socket 110 with respect to the liner 120 by adjusting the spacing between the first and second rollers 134, 136.

The tension member 150 can be controlled by a control mechanism 151 operated by the user. The control mechanism 151 can include a cable or other mechanical system coupled to the tension member 150 and/or first or second rollers 134, 136, such that manipulation of the control mechanism 151 adjusts the location of the roller housings. For example, the control mechanism 151 can be used to adjust the coupler 154 thereby adjusting the location of the second roller housing 140 with respect to the socket 110. In another example, the control mechanism 151 can adjust the location of the first roller housing 138 with respect to the socket 110. The control mechanism 151 can be coupled to the socket 110 at a location other than the location of the attachment mechanism 130. For example, where the control mechanism 151 includes a cable, a distal end of the cable can be coupled to the tension member 150 and/or first or second rollers 134, 136, and the proximal end of the cable can be coupled to the socket 110 at a location remote from the attachment mechanism 130. The portion of the control mechanism 151 that is directly manipulated by the user can be coupled to the socket 110 at a location convenient to the user. For example, the portion of the control mechanism 151 can be coupled to the proximal end of the socket 110, remote from the mechanical limb. In another example, the portion of the control mechanism 151 that is manipulated by the user can be coupled to an article other than the socket 110. For example, the portion of the control mechanism 151 can be coupled to the user's body or to apparel or another device worn by the user.

As outlined above, the first and second roller housings 138, 140 and/or the tension member 150 can be fixedly coupled to the socket 110. For example, the first and second roller housings 138, 140 and/or the tension member 150 can be coupled to the socket 110 using an adhesive or mechanical connection/fastener including, for example, bolts, rivets, screws, and/or any other form of mechanical connection/fastener known in the art. In another example, the first and second roller housings 138, 140 and/or the tension member 150 can be releasably coupled to the socket 110. For example, the first and second roller housings 138, 140 and/or the tension member 150 can be coupled to the socket 110 using a hook, latch, clip, press fit, or any other form of releasable mechanical connection/fastener known in the art.

As illustrated in FIGS. 1, 2 and 5-8, the attachment mechanism 130 can include a locking mechanism 160 for fixing the location of the belt 132 with respect to the socket 110. The locking mechanism 160 can be integrally coupled to roller and/or the roller housing. As illustrated in the example attachment mechanism 130, the second roller 136/second roller housing 140 can including a locking mechanism 160 that engages the belt 132 to fix the location of the belt 132 with respect to the socket 110. It is contemplated that the locking mechanism 160 may be similarly coupled to the first roller 134/first roller housing 138. An example locking mechanism 160 can include a ratchet having a catch and/or pawl coupled to the second roller housing 138 for engaging an inside surface 148 of the belt 132. In another example, the outside surface of the second roller 136 can include a pawl-like and/or catch-like surface for engaging an inside surface 148 of the belt 132. As the pawl/catch engages the belt 132, the location of the belt 132 with respect to the second roller 136, second roller housing 140 and the socket 110 can be fixed. In another example, locking mechanism 160 can include a one-way roller. For example, the second roller 136 can include a one-way roller preventing movement of the belt 132 in a particular direction. The locking mechanism 160 can include a release button 162 for releasing the locking feature of the locking mechanism 160 and thereby permitting movement of the belt 132 with respect to the socket 110. As illustrated in FIGS. 1 and 2, the release button 162 can be located at the proximal end of the socket 110 such that it is conveniently located for the user.

The locking mechanism 160 can be controlled by a control mechanism 161 operated by the user. The control mechanism 161 can be integral with the control mechanism 151 described above with respect to the tension member 150. In another example, the locking mechanism 160 control mechanism 161 can be independent of the tension member 150 control mechanism 151. The control mechanism 161 can include a cable or other mechanical system coupled to the locking mechanism 160 such that manipulation of the control mechanism 161 causes the locking mechanism 160 to release and/or engage the belt 132. For example, the control mechanism 161 can be used to adjust the release button 162 thereby releasing the locking mechanism 160 and permitting movement between the belt 132, the socket 110, and the liner 120. The control mechanism 161 can be coupled to the socket 110 at a location other than the location of the attachment mechanism 130. For example, where the control mechanism 161 includes a cable, a distal end of the cable can be coupled to the locking mechanism 160/release button 162 and the proximal end of the cable can be coupled to the socket 110 at a location remote from the attachment mechanism 130. The portion of the control mechanism 161 that is directly manipulated by the user can be coupled to the socket 110 at a location convenient to the user. For example, the portion of the control mechanism 161 can be coupled to the proximal end of the socket 110, remote from the mechanical limb. In another example, the portion of the control mechanism 161 that is manipulated by the user can be coupled to an article other than the socket 110. For example, the portion of the control mechanism 161 can be coupled to the user's body or to apparel or another device worn by the user.

The prosthetic device 100 can in donned by the user by first applying the liner 120 to their residual limb. The liner-covered limb is then inserted into the socket 110. Applying the socket 110 over the liner-covered limb can include aligning the attachment mechanism 130 with an attachment portion of the liner 120. For example, the user can align the fastener material 122 of the liner 120 with the location corresponding to the belt 132 fastener material 144/attachment mechanism 132. In another example, the liner 120 may include a large portion of fastener material 122 such that alignment between the limb/liner 120 and the socket 110 is not necessary.

As the socket 110 is donned, the fastener material 144 of belt 132 can engage the liner 120 to fix the position of the socket 110 with respect to the liner 120. It is contemplated that as the user is applying the socket 110 and the belt 132 is engaging the liner 120, the belt 132 will move along the first and second rollers 134, 136. For example, as the socket 110 is being donned, the belt 132 will move along the first and second rollers 134, 136 in the direction of the limb.

After the liner-covered limb has been inserted into the socket 110 the location of the limb with respect to the socket 110 can be adjusted. For example, the force on the belt 132 can be adjusted by changing the position of at least one of the first and/or second rollers 134, 136 using the tension member 150. The location of the first roller 134 with respect to the second roller 136 in the longitudinal direction of the socket 110 can impact the force applied on the belt 132. As the tension member 150 is adjusted and the position (i.e., longitudinal spacing) of the first and second rollers 134, 136 is changed, the tension on the belt 132 is adjusted. Similarly, as the position of the first and second rollers 134, 136 is adjusted, the belt 132 moves along the first and second rollers 134, 136 thereby causing a different portion of the belt to contact the liner 120 (as a corresponding portion of the belt 132 releases contact with the liner 120). By adjusting the spacing between the rollers, the user is able to incrementally adjust the location of the socket 110 with respect to the liner 120/limb. As outlined above, function of the tension member 150 and the spacing between the first and second rollers 134, 136 can be manipulated using a corresponding control mechanism 151.

When the socket 110 is a desired location with respect to the liner 120/limb, the user can engage the locking mechanism 160 thereby fixing the location of the belt 132 with respect to the socket 110. The locking mechanism 160 can be released/engaged using the release button 162. As outlined above, function of the locking mechanism 160 can be manipulated using a corresponding control mechanism 161.

The socket 110 can then be coupled to a mechanical limb. It is contemplated that the mechanical limb can be coupled to the socket 110 before it is donned by the user.

To remove the prosthetic device, the user can release the locking mechanism 160 to permit movement of the belt 132 over the rollers and a corresponding movement between the belt 132 and the liner 120. As the liner-covered limb is withdrawn from the socket 110, the belt 132 moves with the liner 120 and release the liner 120 as it is drawn into the opening 116 at the proximal end of the socket 110. Gradually, the belt 132 is completely released from the liner 120 and the user can freely remove their limb from the socket 110. The liner 120 can be removed the limb.

One or more components of the prosthetic device 100 may be made from any biocompatible material known including, for example, plastics, metals such as stainless steel, aluminum, titanium and titanium alloys. Other materials include, for example, composites, polymers, and any other materials suitable for the socket 110 and liner 120.

While the foregoing description and drawings represent the preferred embodiment of the present invention, it will be understood that various additions, modifications, combinations and/or substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. The presently disclosed embodiments are, therefore, to be considered in all respects as illustrative and not restrictive, the scope of the invention being indicated by the appended claims and not limited to the foregoing description.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention, as defined by the following claims.

What is claimed is:

1. A prosthetic device including:
    a liner sized and configured to be worn over a user's residual limb;
    a prosthetic socket sized and configured to be worn over the liner; and
    an attachment mechanism comprising a belt guided over rollers located on an outer surface of the prosthetic socket, each of the rollers are coupled to a roller housing, each of the roller housings coupled to the outer surface of the prosthetic socket,
    wherein a portion of the belt passes from the outer surface of the prosthetic socket to an inner surface of the prosthetic socket to contact the liner,
    wherein the belt matingly engages the liner to fix a position of the prosthetic socket with respect to the liner,
    wherein at least one of the rollers and the corresponding roller housing is coupled to a tension member such that the roller housing is movable in a longitudinal direction along the prosthetic socket to adjust a force applied on the belt at each of the rollers.

2. The attachment mechanism of claim 1, wherein the tension member comprises a tension base and a coupler, the tension base coupled to the outer surface of the prosthetic socket and the coupler matingly engaged with the tension base and movably engaged with the roller housing.

3. The attachment mechanism of claim 2, wherein the coupler movably engages the roller housing to adjust the distance between each of the rollers.

4. The attachment mechanism of claim 2, wherein the coupler is adjusted to reduce a longitudinal distance between the tension base and the corresponding roller housing of the at least one roller, thereby increasing the distance between the rollers.

5. The attachment mechanism of claim 1, wherein the tension member is controlled by a control mechanism operated by the user.

6. The attachment mechanism of claim 5, wherein the control mechanism includes a cable coupled to the tension member such that adjustment of the cable causes the tension member to adjust the location of the roller housing.

7. The attachment mechanism of claim 5, where in the control mechanism is coupled to the prosthetic socket at a location other than the location of the attachment mechanism.

8. The attachment mechanism of claim 1, wherein the force is a tension force applied by separation of the rollers in the longitudinal direction.

9. The attachment mechanism of claim 1, wherein at least one of the rollers and the corresponding roller housing include a locking mechanism that engages the belt to fix the location of the belt with respect to the prosthetic socket.

10. The attachment mechanism of claim 9, wherein the locking mechanism comprises a ratchet, the ratchet including a pawl coupled to the roller housing for engaging an inside surface of the belt.

11. The attachment mechanism of claim 10, wherein the locking mechanism comprises a one-way roller, such that the at least one roller is the one-way roller.

12. The attachment mechanism of claim 10, wherein the locking mechanism includes a release button for releasing the locking mechanism and permitting movement of the belt with respect to the prosthetic socket.

13. The attachment mechanism of claim 9, wherein the locking mechanism is controlled by a control mechanism operated by the user.

14. The attachment mechanism of claim 13, wherein the control mechanism includes a cable coupled to the locking mechanism such that adjustment of the cable causes the locking mechanism to engage and release the belt.

15. The attachment mechanism of claim 13, wherein the control mechanism is coupled to the prosthetic socket at a location other than the location of the attachment mechanism.

16. The attachment mechanism of claim 1, wherein the belt matingly engages the liner to fix the position of the prosthetic socket with respect to the liner in a longitudinal direction.

17. The attachment mechanism of claim 1, wherein the belt matingly engages the liner to fix the position of the prosthetic socket with respect to the liner in a rotational direction.

18. The attachment mechanism of claim 1, wherein the belt includes a fastener material for mating with a corresponding fastener material of the liner,
  wherein the fastener material is a hook and loop material.

19. The attachment mechanism of claim 1, wherein a mechanical limb is coupled to the prosthetic socket,
  wherein the mechanical limb is a lower extremity mechanical limb.

* * * * *